United States Patent [19]

Brunetti et al.

[11] 4,105,626
[45] Aug. 8, 1978

[54] DERIVATIVES OF 4-OXOPIPERIDINES AND THEIR USE AS POLYMER STABILIZERS

[75] Inventors: Heimo Brunetti, Reinach; Jean Rody, Basel, both of Switzerland; Nobuo Soma; Tomoyuki Kurumada, both of Tokyo, Japan

[73] Assignees: Ciba-Geigy Corporation, Ardsley, N.Y.; Sankyo Company, Limited, Tokyo, Japan

[21] Appl. No.: 687,774

[22] Filed: May 19, 1976

[30] Foreign Application Priority Data

May 28, 1975 [GB] United Kingdom ............... 23228/75

[51] Int. Cl.$^2$ .......................... C08K 5/34; C08K 5/35; C07D 491/10
[52] U.S. Cl. .................... 260/45.8 NZ; 260/45.7 PH; 260/45.85 B; 260/293.58; 260/293.66; 526/6
[58] Field of Search ..................... 260/45.8 N, 293.58, 260/293.66, 45.8 NZ

[56] References Cited

U.S. PATENT DOCUMENTS

| | | | |
|---|---|---|---|
| 3,790,525 | 2/1974 | Murayama et al. | 260/45.8 N |
| 3,839,273 | 10/1974 | Murayama et al. | 260/45.8 NZ |
| 3,859,293 | 1/1975 | Murayama et al. | 260/45.8 N |
| 3,899,464 | 8/1975 | Murayama et al. | 260/45.8 N |
| 4,007,158 | 2/1977 | Murayama et al. | 260/45.8 NZ |

OTHER PUBLICATIONS

Murayama et al. — Chem. Abs. 82, 73923f (1975).

*Primary Examiner*—Donald E. Czaja
*Assistant Examiner*—R. A. White
*Attorney, Agent, or Firm*—Vincent J. Cavalieri

[57] ABSTRACT

Cyclic ketals of sterically hindered 4-oxopiperidines are effective light-stabilizers for organic polymers. These compounds have at least five alkyl groups in ring positions 2,3,5 and 6 and four alkyl groups in ring positions 2 and 6, preferably methyl and ethyl groups. The ring nitrogen may be unsubstituted or substituted with a monvalent substitutent. The new compounds can be synthesized by ketalization of the corresponding 4-oxopiperidines with diols, triols or tetrols. Using triols the obtained ketals possess hydroxyl groups which may be esterified or etherified in a subsequent reaction step. Ketalization with tetrols yields cyclic bis-ketals.

24 Claims, No Drawings

DERIVATIVES OF 4-OXOPIPERIDINES AND THEIR USE AS POLYMER STABILIZERS

This invention relates to new derivatives of 4-oxopiperidines, more particulary it relates to cyclic ketals of higher alkylated 4-oxopiperidines and their use as stabilizers for organic polymers against light-induced deterioration.

In the U.S. Pat. No. 3,790,525 there are disclosed ketals of 2,2,6,6-tetramethyl-4-oxopiperidine having the formula

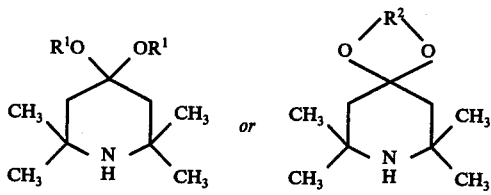

wherein $R^1$ represents alkyl having 1–8 C-atoms and $R^2$ represents alkylene having 2 or 3 C-atoms or o-phenylene.

Similar derivatives of tetramethyl-4-oxopiperidine are disclosed in the British Pat. No. 1.337.600 dealing with compounds

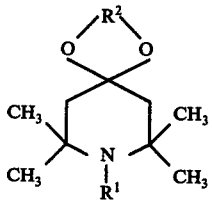

wherein $R^1$ represents alkyl, alkenyl, alkinyl, aralkyl, hydroxyethyl or acyloxyethyl.

Further similar piperidone ketals are disclosed in the German Offenlegungsschriften No. 2,353,538 and 2,433,639. All these known piperidone ketals are derivatives of 2,2,6,6-tetramethyl-4-oxopiperidine and they are known to be stabilizers for polymers especially against photo-deterioration.

Ketal derivatives of piperidones having alkyl groups higher than methyl in 2- and 6-position and alkyl groups in 3- or/and 5-position of the piperidine ring have not hitherto become known.

It has been found now that such ketals of higher alkylated 4-piperidones are valuable stabilizers for organic polymers normally subject to deterioration by light. The new ketals are defined by the formula I

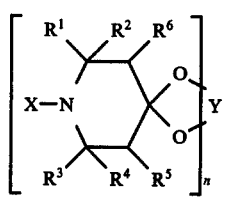

wherein
$n$ is 1 or 2,
$R^1$ is alkyl having 2–6 C-atoms,
$R^2$ is alkyl having 1–6 C-atoms,
$R^3$ is alkyl having 1–9 C-atoms, phenyl, benzyl or phenylethyl,
$R^4$ is alkyl having 1–6 C-atoms, or
$R^3$ and $R^4$ together with the C-atom to which they are attached represent a cyclopentyl or cyclohexyl group,
$R^5$ is alkyl having 1–5 C-atoms, alkenyl or alkinyl having 3–4 C-atoms or aralkyl having 7–8 C-atoms,
$R^6$ is hydrogen, alkyl having 1–5 C-atoms, alkenyl or alkinyl having 3–4 C-atoms, aralkyl having 7–8 C-atoms, and
$R^5$ and $R^6$ are interchangeable,
X is hydrogen, the oxyl radical, alkyl having 1–8 C-atoms, alkenyl having 3–6 C-atoms, alkinyl having 3–6 C-atoms, alkoxyalkyl having 2–21 C-atoms, aralkyl having 7–8 C-atoms, the 2,3-epoxypropyl group, an aliphatic acyl group having 1–12 C-atoms, or one of the groups —$CH_2COOR^7$, —$CH_2$—$CH(R^8)$—$OR^9$ or —$COOR^{10}$ wherein
$R^7$ is alkyl having 1–12 C-atoms, alkenyl having 3–6 C-atoms, phenyl, aralkyl having 7–8 C-atoms or cyclohexyl,
$R^8$ is H, $CH_3$ or phenyl,
$R^9$ is H or an aliphatic, aromatic, araliphatic or alicyclic acyl group having up to 18 C-atoms, which may optionally be substituted in its aryl moiety with chlorine, alkyl having 1–4 C-atoms, alkoxy having 1–8 C-atoms and/or hydroxy,
$R^{10}$ is alkyl having 1–12 C-atoms, benzyl, phenyl or cyclohexyl and if $n$ is 1,
Y is one of the groups —$C(R^{11})(R^{12})$—$CH(R^{13})$—, o-phenylene,
—$CH(R^{11})$—$CH_2$—$C(R^{12})(R^{13})$—, —$CH(R^{12})$—$CH_2$—$C(R^{11})(R^{13})$—,
—$CH_2$—$C(R^{11})(R^{12})$—$CH(R^{13})$—,
wherein $R^{11}$ is hydrogen, methyl or —$CH_2OR^{14}$,
$R^{12}$ is hydrogen, methyl or ethyl,
$R^{13}$ is hydrogen, methyl or ethyl,
$R^{14}$ is hydrogen or a monovalent acyl residue derived from an aliphatic, cycloaliphatic, aromatic or araliphatic monocarboxylic acid having up to 18 C-atoms, which may be substituted in its aryl moiety with halogen, hydroxy and/or lower alkyl groups, or $R^{14}$ is alkyl having 1–4 C-atoms, alkenyl having 3 or 4 C-atoms, benzyl or a carbamoyl residue —CO—NH—$R^{15}$ wherein $R^{15}$ is alkyl having 1–12 C-atoms, cyclohexyl, aralkyl having 7 or 8 C-atoms or aryl having 6–12 C-atoms, and if $n$ is 2
Y is one of the groups

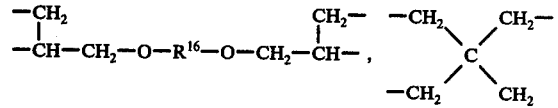

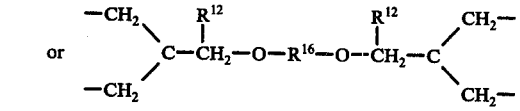

wherein $R^{16}$ is a divalent acyl residue derived from an aliphatic, aromatic or araliphatic dicarboxylic acid having up to 12 C-atoms or $R^{16}$ is a dicarbamoyl residue —CONH—$R^{17}$—NHCO—, wherein $R^{17}$ is alkylene having 2–8 C-atoms, arylene having 6–12 C-atoms, xylylene or methanediphenylene.

Also mixtures of isomers thereof and acid addition salts thereof as suitable as stabilisers.

$R^1$, $R^2$ and $R^4$ may be straight- or branched-chain alkyl groups having 2 to 6 C-atoms such as ethyl, propyl, butyl, iso-butyl, iso-pentyl or n-hexyl; $R^2$ and $R^4$ may also be methyl.

$R^3$ may be a straight- or branched-chain alkyl group having 1 to 9 C-atoms, e.g., methyl, ethyl, propyl, n-butyl, iso-butyl, iso-pentyl, n-hexyl, 2-ethylhexyl, n-nonyl or isononyl.

$R^5$ and $R^6$ may be alkyl groups having up to 5 C-atoms like methyl, ethyl, isopropyl, iso-butyl, n-pentyl. Preferably $R^5$ contains one C-atom less than $R^1$ and $R^6$ contains one C-atom less than $R^2$ and $R^5$ and $R^6$ are interchangeable.

$R^5$ or $R^6$ may be an alkenyl or alkinyl group, for example allyl, methallyl, 2-butenyl or propargyl, especially allyl. $R^5$ and $R^6$ may be an aralkyl group such as benzyl, phenylethyl or methylbenzyl, preferably benzyl.

When X is an alkyl group having from 1 to 8 carbon atoms it may be e.g., methyl, ethyl, n-propyl, n-butyl, n-hexyl or n-octyl; especially an alkyl group having from 1 to 4 carbon atoms and most preferably methyl.

When X is an alkenyl group having from 3 to 6 carbon atoms it may be e.g., allyl, 2-butenyl or 2-hexenyl; especially an alkenyl group having 3 or 4 carbon atoms, most especially allyl.

When X is an alkinyl group having from 3 to 6 carbon atoms it may be e.g. 3-propinyl.

When X is an alkoxyalkyl group having from 2 to 21 C-atoms, it may have from 1 to 3 carbon atoms in its alkyl moiety and from 1 to 18 carbon atoms in its alkoxy moiety, e.g., methoxymethyl, ethoxymethyl, 2-methoxyethyl, 2-ethoxyethyl, 2-n-butoxyethyl, 3-n-butoxypropyl, 2-octoxyethyl or 2-octadecyloxyethyl, especially an alkoxyalkyl group having altogether from 2 to 6 carbon atoms. When X is an aralkyl group having 7 or 8 carbon atoms it may be e.g. benzyl or phenylethyl, especially benzyl.

When X is a group of the formula —$CH_2$—$COOR^7$, $R^7$ may be an alkyl group having from 1 to 12 carbon atoms, e.g., methyl, ethyl, isopropyl, n-butyl, isobutyl, tert.butyl, isopentyl, octyl, decyl or dodecyl, an alkenyl group having 3–6 C-atoms, e.g., allyl, methallyl or 2-hexenyl, a phenyl group, an aralkyl group having 7 or 8 carbon atoms, e.g., benzyl or phenylethyl, or a cyclohexyl group, especially an alkyl group from 1 to 4 carbon atoms.

When X is a group of the formula —$CH_2$—CH($R^8$)—$OR^9$, $R^8$ may be a hydrogen atom, a methyl group or phenyl group, preferably hydrogen, and $R^9$ may be a hydrogen atom or an aliphatic, aromatic, araliphatic or alicyclic acyl group having up to 18 carbon atoms, for example $R^9$ may be an acetyl, propionyl, butyryl, octanoyl, dodecanoyl, stearoyl, acryloyl, benzoyl, chlorobenzoyl, toluoyl, isopropylbenzoyl, 2,4-dichlorobenzoyl, 4-methoxybenzoyl, 3-butoxybenzoyl, 2-hydroxybenzoyl, 3,5-di-tert.butyl-4-hydroxybenzoyl, β(3,5-di-tert-.butyl-4-hydroxyphenyl)propionyl, phenylacetyl, cinnamoyl, hexahydrobenzoyl, 1- or 2-napthoyl or decahydronaphthoyl group.

When X is an aliphatic acyl group having up to 12 carbon atoms, it may be e.g. a formyl, acetyl, acryloyl, crotonoyl, capryloyl or lauroyl group.

When X is a group of the formula —$COOR^{10}$, $R^{10}$ may be an alkyl group having from 1 to 12 carbon atoms, e.g., methyl, ethyl, isobutyl, octyl, decyl or dodecyl, a phenyl group, a benzyl group or a cyclohexyl group.

$R^{14}$ may be a monovalent acyl residue derived from an aliphatic, cycloaliphatic, aromatic or araliphatic monocarboxylic acid having up to 18 C-atoms, which may be substituted in its aryl moiety with halogen, hydroxy and/or lower alkyl groups, e.g., from acetic, propionic, butyric, acrylic, crotonic, capronic, caprylic, lauric, oleic, stearic, benzoic, hexahydrobenzoic, 4-chlorobenzoic, 4-tert.butylbenzoic, 3-methylbenzoic, 4-hydroxy-3,5-di-tert.butyl-benzoic, naphthoic, phenylacetic, phenylpropionic or 4-hydroxy-3,5-di-tert-.butylphenylpropionic acid. $R^{14}$ may also be a lower alkyl group, e.g., methyl, ethyl, propyl, butyl or isopropyl, or it may be an alkenyl group having 3 or 4 C-atoms like allyl or methallyl. When $R^{14}$ is a carbamoyl residue —CONH—$R^{15}$, $R^{15}$ may be alkyl having up to 12 C-atoms, e.g., methyl, ethyl, propyl, isobutyl, n-hexyl, 2-ethylhexyl, n-octyl, n-decyl or n-dodecyl, $R^{15}$ may be aralkyl having 7 or 8 C-atoms, like benzyl or phenethyl or $R^{15}$ may be aryl having 6–12 C-atoms, e.g., phenyl, tolyl or naphthyl.

$R^{16}$ is a divalent residue and it may be a diacyl residue derived from an aliphatic, aromatic or araliphatic dicarboxylic acid having up to 12 C-atoms, e.g., from malonic, maleic, succinic, adipic, sebacic, isophthalic, terephthalic, naphthalene-1,5-dicarboxylic, diphenyl-4,4'-dicarboxylic or p-xylylene-dicarboxylic acid, or $R^{16}$ may be a dicarbamoyl residue —CONH—$R^{17}$—NH-CO—, wherein $R^{17}$ is alkylene having 2–8 C-atoms, e.g., ethylene, tetramethylene, hexamethylene or octamethylene, or $R^{17}$ is arylene having 6–12 C-atoms, e.g., phenylene, 2,5-dimethyl-1,4-phenylene, 4,4'-diphenylene or 4,4'-diphenylene oxide, or $R^{17}$ is a xylylene or a methane-diphenylene residue.

The 4-piperidinone derivatives having the aforementioned general formula I possess assymmetric carbon atoms. Accordingly, by the term "mixture of isomers thereof" are meant mixtures of position isomers at 3- and 5-position and/or various kinds of stereo isomers. At any stage of the synthesis of the compounds according to the invention, the misture of isomers usually obtained in the preparation of the corresponding 4-piperidinones which are used as starting material, can be separated by methods known per se.

Preferred are compounds of formula I wherein $R^1$ and $R^3$ represent ethyl groups, $R^2$, $R^4$ and $R^5$ represent methyl groups, $R^6$ represents hydrogen, X represents a hydrogen atom, a methyl, acetyl, acryloyl or crotonyl group and n is 1 and Y is a group —$CH_2$—CH($R^{11}$)— or —$CH_2$—C($R^{11}$)($R^{12}$)—$CH_2$—, wherein $R^{11}$ is H, $CH_3$ or $CH_2OR^{14}$, $R^{12}$ is H, $CH_3$ or $C_2H_5$ and $R^{14}$ is H, an aliphatic acyl residue having 2–12 C-atoms or a benzoyl residue, which may be substituted with alkyl having 1–4 C-atoms and/or hydroxyl, or $R^{14}$ is a β(3,5-di-tert.butyl-4-hydroxyphenyl) propionyl group, or n is 2 and Y is the group (—$CH_2$)$_2$C($CH_2$—)$_2$.

The following is a list of individual ketals of formula I. It is, however, to be understood that the present invention is not limited to these compounds.

8-aza-6,7,9-trimethyl-7,9-diethyl-1,4-dioxaspiro [4.5] decane 8-aza-6,7,8,9-tetramethyl-7,9-diethyl-1,4-dioxaspiro [4.5] decane 8-aza-8-allyl-6,7,9-trimethyl-7,9-diethyl-1,4-dioxaspiro [4.5] decane 8-aza-6,7,9-trimethyl-7,9-diethyl-1,4-dioxaspiro [4.5] decane-8-oxyl 8-aza-8-benzyl-6,7,9-trimethyl-7,9-diethyl-1,4-dioxaspiro [4.5] decane 8-aza-8-(2-hydroxyethyl)-6,7,9-trimethyl-7,9-diethyl-1,4-dioxaspiro [4.5] decane 8-aza-8-(2-benzoyloxyethyl)-6,7,9-trimethyl-7,9-diethyl-1,4-dioxaspiro [4.5] decane 8-aza-8-butyl -6,7,9-trimethyl-7,9-diethyl-1,4-dioxaspiro [4.5] decane 8-aza-8-ethoxycarbonylmethyl-6,7,9-trimethyl-7,9-diethyl-1,4-dioxaspiro [4.5] decane 8-aza-7,7,9,9-tetraethyl-6,10-dimethyl-1,4-dioxaspiro [4.5] decane 8-aza-7,9-dipropyl-7,9-dimethyl -6-ethyl-1,4-dioxaspiro [4.5] decane 8-aza-7,9-diisobutyl-7,9-dimethyl-6-isopropyl-1,4-dioxaspiro [4.5] decane 8-aza-7,9-diisopentyl-7,9-dimethyl-6-isobutyl-1,4-dioxaspiro [4.5] decane 8-aza-7-nonyl-9-ethyl-6,7,9-trimethyl-1,4-dioxaspiro [4.5] decane 8-aza-7,7-di-n-butyl-9-ethyl-6,9-dimethyl-1,4-dioxaspiro [4.5] decane 8-aza-7-phenethyl-9-ethyl-6,7,9-trimethyl-1,4-dioxaspiro [4.5] decane 8-aza-2-hydroxymethyl-6,7,9-trimethyl-7,9-diethyl-1,4-dioxaspiro [4.5] decane 8-aza-2-hydroxymethyl-7,7,9,9-tetraethyl-6,10-dimethyl-1,4-dioxaspiro [4.5] decane 8-aza-2-hydroxymethyl-7,9-dipropyl-7,9-dimethyl -6-ethyl-1,4-dioxaspiro [4.5] decane 8-aza-2-acetoxymethyl-6,7,9-trimethyl-7,9-diethyl-1,4-dioxaspiro [4.5] decane 8-aza-2-acetoxymethyl-6,7,8,9-tetramethyl-7,9-diethyl-1,4-dioxaspiro [4.5] decane 8-aza-2-butyroyloxymethyl-6,7,9-trimethyl-7,9-diethyl-1,4-dioxaspiro [4.5] decane 8-aza-2-acryloyloxymethyl-6,7,9-trimethyl-7,9-diethyl-1,4-dioxaspiro [4.5] decane 8-aza-2-lauroyloxymethyl-6,7,9-trimethyl-7,9-diethyl-1,4-dioxaspiro [4.5] decane 8-aza-2-benzoyloxymethyl-6,7,9-trimethyl-7,9-diethyl-1,4-dioxaspiro [4.5] decane 8-aza-2-p-t-butylbenzoyloxymethyl-6,7,9-trimethyl-7,9-diethyl-1,4-dioxaspiro [4.5] decane 8-aza-2-(3,5-di-t-butyl-4-hydroxybenzoyloxymethyl)-6,7,9-trimethyl-7,9-diethyl-1,4-dioxaspiro [4.5] decane 8-aza-2-[β-(3,5-di-t-butyl-4-hydroxyphenyl)-propionyloxymethyl]-6,7,9-trimethyl-7,9-diethyl-1,4-dioxaspiro [4.5] decane 8-aza-2-stearoyloxymethyl-6,7,9-trimethyl-7,9-diethyl-1,4-dioxaspiro [4.5] decane bis(8-aza-6,7,9-trimethyl-7,9-diethyl-1,4-dioxaspiro [4.5] decyl-2-methyl)succinate bis(8-aza-6,7,9-trimethyl-7,9-diethyl-1,4-dioxaspiro [4.5] decyl-2-methyl)adipate bis(8-aza-6,7,9-trimethyl-7,9-diethyl-1,4-dioxaspiro [4.5] decyl-2-methyl)sebacate bis(8-aza-6,7,8,9-tetramethyl-7,9-diethyl-1,4-dioxaspiro [4.5] decyl-2-methyl)sebacate bis(8-aza-6,7,9-trimethyl-7,9-diethyl-1,4-dioxaspiro [4.5] decyl-2-methyl)terephthalate 8-aza-2,6,7,9-tetramethyl-7,9-diethyl-1,4-dioxaspiro [4.5] decane 8-aza-2,6,7,8,9-pentamethyl-7,9-diethyl-1,4-dioxaspiro [4.5] decane 8-aza-2,6,7,9-tetramethyl-7,9-diethyl-1,4-dioxaspiro [4.5] decane-8-oxyl 8-aza-2,6,7,9-tetramethyl-7,9-diethyl-8-allyl-1,4-dioxaspiro [4.5] decane 8-aza-2,6,10-trimethyl-7,7,9,9-tetraethyl-1,4-dioxaspiro [4.5] decane 8-aza-2,7,9-trimethyl-7,9-dipropyl-6-ethyl-1,4-dioxaspiro [4.5] decane 8-aza-2,7,9-trimethyl-7,9-diisopentyl-6-isobutyl-1,4-dioxaspiro [4.5] decane 8-aza-2,3,6,7,9-pentamethyl-7,9-diethyl-1,4-dioxaspiro [4.5] decane 8-aza-2,3,6,7,8,9-hexamethyl-7,9-diethyl-1,4-dioxaspiro [4.5] decane 9-aza-7,8,10-trimethyl-8,10-diethyl-1,5-dioxaspiro [5.5] undecane 9-aza-7,8,9,10-tetramethyl-8,10-diethyl-1,5-dioxaspiro [5.5] undecane 9-aza-7,8,10-trimethyl-8,10-diethyl-1,5-dioxaspiro [5.5] undecane-9-oxyl 9-aza-7,8,10-trimethyl-8,10-diethyl -9-allyl-1,5-dioxaspiro [5.5] undecane 9-aza-8,10-dimethyl -8,10-dipropyl-7-ethyl-1,5-dioxaspiro [5.5] undecane 9-aza-8,10-dimethyl-8,10-diisobutyl-7-isopropyl-1,5-dioxaspiro [5.5] undecane 9-aza-2,7,8,10-tetramethyl-8,10-diethyl-1,5-dioxaspiro [5.5] undecane 9-aza-2,7,8,9,10-pentamethyl-8,10-diethyl-1,5-dioxaspiro [5.5] undecane 9-aza-2,4,7,8,10-pentamethyl-8,10-diethyl-1,5-dioxaspiro [5.5] undecane 9-aza-2,4,7,8,9,10-hexamethyl-8,10-diethyl-1,5-dioxaspiro [5.5] undecane 9-aza-2,4,7,8,10-pentamethyl-8,10-diethyl-9-benzyl-1,5-dioxaspiro [5.5] undecane 9-aza-3,3,7,8,10-pentamethyl-8,10-diethyl-1,5-dioxaspiro [5.5] undecane 9-aza-3,3,7,8,9,10-hexamethyl-8,10-diethyl-1,5-dioxaspiro [5.5] undecane 9-aza-3,3,7,8,10-pentamethyl-8,10-diethyl-1,5-dioxaspiro [5.5] undecane-9-oxyl 9-aza-3,3,7,11-tetramethyl-8,8,10,10-tetraethyl-1,5-dioxaspiro [5.5] undecane 9-aza-3,3,8,10-tetramethyl-8,10-dipropyl-7-ethyl-1,5-dioxaspiro [5.5] undecane 9-aza-3,3,8,10-tetramethyl-8,10-diisobutyl-7-isopropyl-1,5-dioxaspiro [5.5] undecane 9-aza-3,3,8,10-tetramethyl-8,10-diisopentyl-7-isobutyl-1,5-dioxaspiro [5.5] undecane 9-aza-3,7,8,10-tetramethyl-3,8,10-triethyl-1,5-dioxaspiro [5.5] undecane 9-aza-3,7,8,9,10-pentamethyl-3,8,10-triethyl-1,5-dioxaspiro [5.5] undecane 9-aza-3,7,8,10-tetramethyl-3,8,10-triethyl-1,5-dioxaspiro [5.5] undecane-9-oxyl 9-aza-3-hydroxymethyl-3,7,8,10-tetramethyl-8,10-diethyl-1,5-dioxaspiro [5.5] undecane 9-aza-3-hydroxymethyl-3,8,10-trimethyl-8,10-dipropyl-7-ethyl-1,5-dioxaspiro [5.5] undecane 9-aza-3-hydroxymethyl-3,7,11-trimethyl-8,8,10,10-tetraethyl-dioxaspiro [5.5] undecane 9-aza-3-hydroxymethyl-3,8,10-trimethyl-8,10-diisobutyl-7-isopropyl-dioxaspiro [5.5] undecane 9-aza-3-hydroxymethyl-3,8,10-trimethyl-8,10-diisopentyl-7-isobutyl-dioxaspiro [5.5] undecane 9-aza-3-hydroxymethyl-7,8,10-trimethyl-3,8,10-triethyl-1,5-dioxaspiro[5.5]undecane 9-aza-3-hydroxymethyl-8,10-dimethyl-8,10-dipropyl-3,7-diethyl-1,5-dioxaspiro[5.5]undecane
9-aza-3-hydroxymethyl-8,10-dimethyl-8,10-diisobutyl-3-ethyl-7-isopropyl-1,5-dioxaspiro[5.5]undecane
9-aza-3-hydroxymethyl-8,10-dimethyl-8,10-diisopentyl-3-ethyl-7-isobutyl-1,5-dioxaspiro[5.5]undecane
9-aza-3-acetoxymethyl-3,7,8,10-tetramethyl-8,10-diethyl-1,5-dioxaspiro[5.5]undecane
9-aza-3-acetoxymethyl-3,7,8,9,10-pentamethyl-8,10-diethyl-1,5-dioxaspiro[5.5]undecane
9-aza-3-lauroyloxymethyl-3,7,8,10-tetramethyl-8,10-diethyl-1,5-dioxaspiro[5.5]undecane
9-aza-3-stearoyloxymethyl-3,7,8,10-tetramethyl-8,10-diethyl-1,5-dioxaspiro[5.5]undecane
9-aza-3-benzoyloxymethyl-3,7,8,10-tetramethyl-8,10-diethyl-1,5-dioxaspiro[5.5]undecane
9-aza-3-p-t-butylbenzoyloxymethyl-3,7,8,10-tetramethyl-8,10-diethyl-1,5-dioxaspiro[5.5]undecane
9-aza-3-(3,5-di-t-butyl-4-hydroxybenzoyloxymethyl)-3,7,8,10-tetramethyl-8,10-diethyl-1,5-dioxaspiro[5.5]undecane
9-aza-3-[β-(3,5-di-t-butyl-4-hydroxyphenyl)-propionyloxymethyl]-3,7,8,10-tetramethyl-8,10-diethyl-1,5-dioxaspiro[5.5]undecane
bis(9-aza-3,7,8,10-tetramethyl-8,10-diethyl-1,5-dioxaspiro[5.5]-3-undecylmethyl)succinate
bis(9-aza-3,7,8,10-tetramethyl-8,10-diethyl-1,5-dioxaspiro[5.5]-3-undecylmethyl)adipate
bis(9-aza-3,7,8,10-tetramethyl-8,10-diethyl-1,5-dioxaspiro[5.5]-3-undecylmethyl)sebacate
bis(9-aza-3,7,8,10-tetramethyl-8,10-diethyl-1,5-dioxaspiro[5.5]-3-undecylmethyl)terephthalate
9-aza-3-acetoxymethyl-7,8,10-trimethyl-3,8,10-triethyl-1,5-dioxaspiro[5.5]undecane
9-aza-3-benzoyloxymethyl-7,8,10-trimethyl-3,8,10-triethyl-1,5-dioxaspiro[5.5]undecane
9-aza-3-benzoyloxymethyl-7,8,9,10-tetramethyl-3,8,10-triethyl-1,5-dioxaspiro[5.5]undecane
9-aza-3-lauroyloxymethyl-7,8,10-trimethyl-3,8,10-triethyl-1,5-dioxaspiro[5.5]undecane
9-aza-3-(3,5-di-t-butyl-4-hydroxybenzoyloxymethyl)-7,8,10-trimethyl-3,8,10-triethyl-1,5-dioxyspiro[5.5]undecane
9-aza-3-[β-(3,5-di-t-butyl-4-hydroxyphenyl)-propionylmethyl]-7,8,10-trimethyl-3,8,10-triethyl-1,5-dioxaspiro[5.5]undecane
bis(9-aza-7,8,10-trimethyl-3,8,10-triethyl-1,5-dioxaspiro[5.5]undecyl-3-methyl)adipate
bis(9-aza-7,8,10-trimethyl-3,8,10-triethyl-1,5-dioxaspiro[5.5]undecyl-3-methyl)sebacate
bis(9-aza-7,8,10-trimethyl-3,8,10-triethyl-1,5-dioxaspiro[5.5]undecyl-3-methyl)terephthalate
2,6-diethyl-2,3,6-trimethylpiperidine-4-spiro-2'-(1',3'-dioxane)-5'-spiro-5''-(1'',3''-dioxane)-2''-spiro-4'''-(2''',6'''-diethyl-2''',3''',6'''-trimethylpiperidine)
2,6-diethyl-1,2,3,6-tetramethylpiperidine-4-spiro-2'-(1',3'-dioxane)-5'-spiro-5''-(1'',3''-dioxane)-2''-spiro-4'''-(2''',6'''-diethyl-1''',2''',3''',6'''-tetramethylpiperidine)
1-allyl-2,6-diethyl-2,3,6-trimethylpiperidine-4-spiro-2'-(1',3'-dioxane)-5'-spiro-5''-(1'',3''-dioxane)-2''-spiro-4'''-(1'''-allyl-2''',6'''-diethyl-2''',3''',6'''-trimethylpiperidine)
1-benzyl-2,6-diethyl-2,3,6-trimethylpiperidine-4-spiro-2'-(1',3'-dioxane)-5'-spiro-5''-(1'',3''-dioxane)-2''-spiro-4'''-(1'''-benzyl-2''',6'''-diethyl-2''',3''',6'''-trimethylpiperidine)
1-(2-hydroxyethyl)-2,6-diethyl-2,3,6-trimethylpiperidine-4-spiro-2'-(1',3'-dioxane)-5'-spiro-5''-(1'',3''-dioxane)-2''-spiro-4'''-[1''''-(2-hydroxyethyl)-2''',6'''-diethyl-2''',3''',6'''-trimethylpiperidine]
1-(2-acetoxyethyl)-2,6-diethyl-2,3,6-trimethylpiperidine-4-spiro-2'-(1',3'-dioxane)-5'-spiro-5''-(1'',3''-dioxane)-2''-spiro-4'''-[1''''-(2-acetoxyethyl)-2''', 6'''-diethyl-2''',3''',6'''-trimethylpiperidine]
1-(2-benzoyloxyethyl)-2,6-diethyl-2,3,6-trimethylpiperidine-4-spiro-2'-(1',3'-dioxane)-5'-spiro-5''-(1'',3''-dioxane)-2''-spiro-4'''-[1''''-2-benzoyloxyethyl)-2''',6'''-diethyl-2''',3''',6'''-trimethylpiperidine]
2,6-dimethyl-2,6-dipropyl-3-ethylpiperidine-4-spiro-2'-(1',3'-dioxane)-5'-spiro-5''-(1'',3''-dioxane)-2''-spiro-4'''-(2''',6'''-dimethyl-2''',6'''-dipropyl-3'''-ethylpiperidine)
2,6-dimethyl-2,6-diisobutyl-3-isopropylpiperidine-4-spiro-2'-(1',3'-dioxane)-5'-spiro-5''-(1'',3''-dioxane)-2''-spiro-4'''-(2''',6'''-dimethyl-2''',6'''-diisobutyl-3'''-isopropylpiperidine)
2,6-dimethyl-2,6-diisopentyl-3-isobutylpiperidine-4-spiro-2'-(1',3'-dioxane)-5'-spiro-5''-(1'',3''-dioxane)-2''-spiro-4'''-(2''',6'''-dimethyl-6'''-diisopentyl-5-isobutylpiperidine)
8-aza-8-acetyl-2,6,7,9-tetramethyl-7,9-diethyl-1,4-dioxaspiro[4.5]decane
8-aza-8-acetyl-6,7,9-trimethyl-7,9-diethyl-1,4-dioxaspiro[4.5]decane
8-aza-8-acryloyl-6,7,9-trimethyl-7,9-diethyl-1,4-dioxaspiro[4.5]decane
8-aza-8-acetyl-2-acetoxymethyl-6,7,9-trimethyl-7,9-diethyl-1,4-dioxaspiro[4.5]decane
8-aza-8-acryloyl-2-acryloyloxymethyl-6,7,9-trimethyl-7,9-diethyl-1,4-dioxaspiro[4.5]decane
9-aza-9-acetyl-7,8,10-trimethyl-8,10-diethyl-1,5-dioxaspiro[5.5]decane
9-aza-9-acetyl-3-acetoxymethyl-3,7,8,10-tetramethyl-8,10-diethyl-1,5-dioxaspiro[5.5]undecane
1-acetyl-2,6-diethyl-2,3,6-trimethylpiperidine-4-spiro-2'-(1',3'-dioxane)-5'-spiro-5''-(1'',3''-dioxane)-2''-spiro-4'''-(1'''-acetyl-2''',6'''-diethyl-2''',3''',6'''-trimethylpiperidine)
8-aza-8-crotonoyl-6,7,9-trimethyl-7,9-diethyl-1,4-dioxaspiro[4.5]decane.

The ketals of formula I can be prepared from the corresponding 4-oxopiperidines (II) by reaction with polyols $Y(OH)_{2n}$ with acidic catalysis in the manner generally known for the preparation of cyclic ketals:

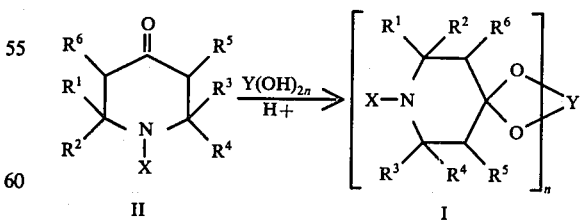

The 4-oxopiperidines of formula II can be prepared by reacting an aliphatic ketone, this being a higher homologue of aceton, with ammonia. For example 2,3,6-trimethyl-2,6-diethyl-4-oxopiperidine is obtained from methyl ethyl ketone and ammonia, as is described by W. Traube in Chem.Berichte 41 (1908), 777.

Another method of synthesis is the hydrolysis of alkyl-substituted tetrahydropyrimidines in the presence of acidic catalysts, for example analogously to the process of U.S. Pat. No. 3,513,170.

Compounds of formula II having different substituents in 2- and 6-position are obtainable by first reacting a ketone $R^1$—CO—$R^2$ with ammonia and hydrolysing the formed pyrimidine derivative resulting in the formation of an amino ketone

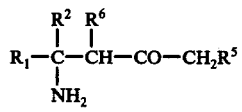

as is described in Helvet. Chim. Acta 30, (1947), 1114. In a second step this aminoketone is reacted with ammonia and a second ketone $R^3$—CO—$R^4$ resulting in a pyrimidine derivative as is described in Monatsh. Chemie 88 (1957), 464. From this the piperidone derivative II can be obtained by hydrolysis.

Such and similar methods of preparing alkylated 4-piperidones are further described in German laid open patent applications 2,429,745; 2,429,746; 2,429,935; 2,429,936; 2,429,937.

The introduction of the substituent X may be achieved with the ketones of formula II or with the ketals of formula I, when in both formulae X is H, by methods generally known for the alkylation and acylation of secondary amines. Thus the NH-compounds may be reacted e.g. with alkyl, alkenyl, aralkyl or alkoxyalkyl halides, with dialkyl sulfates, with epichlorohydrine, with esters of chloroacetic acid, with esters of chlorocarbonic acid, with carboxylic acid chlorides or anhydrides. The introduction of a group —$CH_2$—$CH(R^8)$—$OR^9$ is achieved by reaction with ethylene oxide, propylene oxide or styrene oxide, which may be followed by acylation, e.g. with an acyl chloride $R^9Cl$.

The introduction of an acyl residue as $R^{14}$ or $R^{16}$ may be achieved by acylation of the ketals of formula I, carrying in the ketal group Y a methylol group —$CH_2OH$, by methods generally known for the acylation of hydroxyl compounds, e.g., by reaction with mono- or dicarboxylic acid chlorides or anhydrides. Alternatively compounds of formula I having an acyloxymethyl group in the ketal group Y may also be prepared by ketalisation of a 4-oxopiperidine II with an acyloxymethyldiol e.g., with glycerol 1-monostearate or 1,1,1-trimethylolpropane monopropionate.

If $R^{14}$ and X represent the same acyl residue both substituents may be introduced simultaneously in a one step acylation reaction reaction.

In the same way an ether residue $R^{14}$ may be introduced either by etherification of the methylol ketals, e.g., by reaction with alkyl, alkenyl or benzyl halides, or — preferably — by using ether-diols in the ketalisation reaction.

If $R^{14}$ is a carbamoyl residue or $R^{16}$ is a dicarbamoyl residue these residues may be introduced by reacting the methylol ketals with mono- or diisocyanates.

Compounds of formula I wherein X is the oxyl radical are obtainable from the corresponding NH-compounds by oxydation with percarboxylic acids, e.g., 3-chloroperbenzoic acid, or with hydrogen peroxide in the presence of catalysts like sodium tungstate.

Acid addition salts of the compounds of formula I may be prepared by neutralising the piperidine derivatives with the appropriate acids, preferably in an organic solvent or its mixture with water. The formation of a salt is not possible if X is an acyl or —$COOR^{10}$ group.

In accordance with the invention, it has now been discovered that the cyclic ketals of formula I and acid addition salts thereof can effectively stabilize a wide range of organic polymers against light-induced deterioration with superior compatibility with polymer substrates. Polymers which can be stabilized in this way include:

1. Polymers of mono- and diolefins, e.g. polyethylene which can optionally be crosslinked, polypropylene, polyisobutylene, polymethylbutene-1, polymethylpentene-1, polyisoprene, polybutadiene.

2. Mixtures of the homopolymers cited under 1), for example mixtures of polypropylene and polyethylene or polypropylene and polyisobutylene.

3. Copolymers of mono- and diolefins, for example ethylene/propylene copolymers, propylene/butene-1 copolymers, propylene/isobutylene copolymers, ethylene/butene-1 copolymers as well as terpolymers of ethylene and propylene with a diene, for example hexadiene, dicyclopentadiene or ethylidene norbornene.

4. Polystyrene.

5. Copolymers of styrene and of α-methylstyrene, for example styrene/butadiene copolymers, styrene/acrylonitrile copolymers, styrene/acrylonitrile/methylacrylate copolymers; high impact strength mixtures of styrene/acrylonitrile copolymers with other polymers, e.g. with polyacrylates, diene polymers or ethylene/propylene/diene terpolymers; and block copolymers of styrene, e.g., styrene/butadiene/styrene or styrene/isoprene/styrene block copolymers.

6. Graft copolymers of styrene, for example the graft polymer of styrene to polybutadiene, the graft polymer of styrene with acrylonitrile to polybutadiene as well as mixtures thereof with the copolymers cited under (5), commonly referred to as acrylonitrile/butadiene/styrene or ABS plastics.

7. Halogen-containing vinyl polymers, for example polyvinyl chloride, polyvinylidene chloride, polyvinyl fluoride, polychloroprene, chlorinated rubbers, vinyl chloride/vinylidene chloride copolymers, vinyl chloride/vinyl acetate copolymers, vinylidene chloride/vinyl acetate copolymers.

8. Polymers which are derived from α,β-unsaturated acids and derivatives thereof, polyacrylates and polymethacrylates, polyacrylic amides and polyacrylonitrile.

9. Polymers which are derived from unsaturated alcohols and amines and from the acyl derivatives thereof or acetals, for example polyvinyl alcohol, polyvinyl acetate, polyvinyl stearate, polyvinyl benzoate, polyvinyl maleate, polyvinyl butyral, polyallyl phthalate, polyallyl melamine and copolymers thereof with other vinyl compounds, for example ethylene/vinyl acetate copolymers.

10. Homopolymers and copolymers which are derived from epoxides, for example polyethylene oxide, polypropylene oxide or polyisobutylene oxide.

11. Polyacetals, for example polyoxymethylene, as well as polyoxymethylenes which contain ethylene oxide as comonomer.

12. Polyphenylene oxides.

13. Polyurethanes and polyureas.

14. Polycarbonates.

15. Polysulphones.
16. Polyamides and copolyamides which are derived from diamines and dicarboxylic acids and/or from aminocarboxylic acids or the corresponding lactames, for example polyamide 6, polyamide 6/6, polyamide 6/10, polyamide 11, polyamide 12.
17. Polyesters which are derived from dicarboxylic acids and dialcohols and/or from hydroxycarboxylic acids or the corresponding lactones, for example polyethylene glycol terephthalate, poly-1,4-dimethylol-cyclohexane terephthalate.
18. Cross-linked polymers which are derived from aldehydes on the one hand and from phenols, ureas and melamines on the other, for example phenol/formaldehyde, urea/formaldehyde and melamine/formaldehyde resins.
19. Alkyd resins, for example glycerol/phthalic acid resins and mixtures thereof with melamine/formaldehyde resins.
20. Unsaturated polyester resins which are derived from copolyesters of saturaed and unsaturated dicarboxylic acids with polyhydric alcohols as well as from vinyl compounds as cross-linking agents and also the halogen-containing, flame-resistant modifications thereof.
21. Cross-linked epoxide resins, derives from polyepoxides, e.g. from bis-glycidyl-ethers or from cycloaliphatic diepoxides.
22. Natural polymers, for example cellulose, rubber, proteins as well as the chemically modified homologous derivatives thereof, for example cellulose acetates, cellulose propionates and cellulose butyrates and the cellulose ethers, for example methyl cellulose.

From these the polymers of groups 1–6, 13 and 16 are of particular interest as the application of the stabilizers according to the invention has an outstanding effect on these polymers.

The stabilizer compounds of formula I are added to the polymers in an amount of from 0.01 to 5% by weight, based on the weight of the polymer. Preferably they are added in an amount of from 0.02 to 1.0 and most preferably from 0.05 to 0.5% by weight.

The stabilizers of formula I may readily be incorporated into the organic polymers by conventional techniques, at any convenient stage prior to the manufacture of shaped articles therefrom. For example, the stabilizer may be mixed with the polymer in dry powder form, or a solution or a suspension of the stabilizer may be mixed with a solution or suspension of the polymer.

The stabilized polymer compositions of the invention may optionally also contain other known stabilizers or other additives usually known in plastics technology, such as the additives listed in British patent specification No. 1,401,924, pages 11 to 13.

Synergistic effects may appear in using such known additives in combination with the stabilizers of formula I. This is especially true with other light-stabilizers and with organic phosphites.

Of particular importance is the combination of the light-stabilizers of formula I with antioxydants, especially for the stabilisation of polyolefins.

The invention is further illustrated by the following Examples in which all parts and percentages are by weight.

EXAMPLE 1

98,6 g of 2,6-diethyl-2,3,6-trimethyl-4-oxo-piperidine and 105 g of p-toluenesulfonic acid (monohydrate) are dissolved in 500 ml of toluene and the solution is heated to reflux with separation of the formed water in a separation condenser. After the separation of water has ceased 31 g of ethylene glycol are added and the heating is continued until the calculated amount of water has been separated, which is achieved in about 12 hours. The cooled reaction mixture is washed with 300 ml 2n sodium hydroxide solution and the toluene solution is dried over $Na_2SO_4$ and evaporated to dryness. By distillation of the residue there is obtained 8-aza-6,7,9-trimethyl-7,9-diethyl-1,4-dioxa-spiro[4.5]decane (Compound No. 1) which distills at 92°–94° C at 0.65 mm Hg.

If instead of ethylene glycol the equivalent amounts are used of 1,2-propanediol, 2,2-dimethyl-1,3-propanediol, glycerol, 1,1,1-tris(hydroxymethyl)ethane, 1,1,1-tris(hydroxymethyl)propane, 2-methyl-2-benzyloxymethyl-1,3-propanediol, or pentaerythritol in the procedure as described above there are obtained:

8-aza-2,6,7,9-tetramethyl-7,9-diethyl-1,4-dioxa-spiro[4.5]decane (Compound No. 2), b.p. 75–78/0.04 mm Hg; 9-aza-3,3,7, 8,10-pentamethyl-8,10-diethyl-1,5-dioxaspiro[5.5]undecane (Compound No. 3), b.p. 95°–97° C/0.3 mm Hg; 8-aza-2-hydroxymethyl-6,7,9-trimethyl-7,9-diethyl-1,4-dioxaspiro[4.5]decane (Compound No. 4), b.p. 118° C/0.3 mm Hg; 9-aza-3-hydroxymethyl-3,7,8,10-tetramethyl-8,10-diethyl-1,5-dioxaspiro[5.5]undecane (Compound No. 5), b.p. 163°–165° C/0.2 mm Hg; 9-aza-3-hydroxymethyl-3,8,10-triethyl-7,8,10-trimethyl-1,5-dioxaspiro[5.5]undecane (Compound No. 6), b.p. 151°–152° C/0.06 mm Hg; 9-aza-3-benzyloxymethyl-3,7,8,10-tetramethyl-8,10-diethyl-1,5-dioxa spiro[5.5]undecane (Compound No. 7), b.p. 192°–195° C/0.01 mm Hg; and 2,6-diethyl-2,3,6-trimethylpiperidine-4-spiro-2'-(-1',3'-dioxane)-5'-spiro-5''-(1'',3''-dioxane)-2''-spiro-4'''-(2''',6'''-diethyl-2''',3''',6'''-trimethylpiperidine) (Compound No. 8) as a viscous resin, which can be purified by chromatography from a toluene-methanol mixture 5:1 on silica.

The starting material is obtained as follows:

19.6 g of 2,4,6-triethyl-2,6-dimethyl-1,2,5,6-tetrahydropyrimidine and 0.4 g of ammonium bromide were added to 200 ml of methanol. To the mixture was added dropwise 10 g of 37% hydrochloric acid at 10° C., with stirring. After completion of the addition the whole was stirred at room temperature for 4 hours and there was then added a further 20 ml of 18% hydrochloric acid, The mixture was then heated at 30°–40° C for 7 hours and allowed to stand overnight at room temperature. The mixture was made alkaline with 40% aqueous potassium carbonate solution and, after methanol had been distilled off under reduced pressure, the mixture was extracted with ether. The ether solution was dried over potassium carbonate and the ether was removed. The residue was subjected to distillation under reduced pressure to give 15.1 g of 2,6-diethyl-2,3,6-trimethyl-4-oxopiperidine as an oil boiling at 91°–93° C/2.0 mm Hg.

EXAMPLE 2

34 g of 9-aza-3,3,7,8,10-pentamethyl-8,10-diethyl-1,5-dioxaspiro[5.5]undecane and 20.4 g of methyl iodide are stirred for 20 hours at 45° to 50° C. Afterwards 100 ml of diethyl ether are added and the precipitated hydroiodide is filtered off. The ethereal solution is evaporated and the residue is distilled in vacuo yielding 9-aza- 3,3,7,8,9,10-hexamethyl-8,10-diethyl-1,5-dioxaspiro[5.5]undecane (Compound No. 9) boiling at 92° C/0.03 mm Hg.

EXAMPLE 3

24.1 g of 8-aza-6,7,9-trimethyl-7,9-diethyl-1,4-dioxaspiro[4.5]decane (Compound No. 1), 10 g of triethylamine and 12 g of allyl bromide are dissolved in 60 ml of benzene and stirred 2 hours under reflux. The precipitated hydrobromide is filtered off and washed with benzene. The combined benzene solutions are evaporated in vacuo and the residue is distilled in high-vacuum. There is obtained a distillate consisting of 8-aza-8-allyl-6,7,9-trimethyl-7,9-diethyl-1,4-dioxaspiro[4.5]decane (Compound No. 10), b.p. 132°–135° C/0.2 mm Hg.

In the same manner Compound No. 1 is reacted with 13 g of benzyl chloride yielding 8-aza-8-benzyl-6,7,9-trimethyl-7,9-diethyl-1,4-dioxaspiro[4.5]decane (Compound No. 11), b.p. 180°–182° C/0.3 mm Hg.

EXAMPLE 4

27.1 g of 8-aza-2-hydroxymethyl-6,7,9-trimethyl-7,9-diethyl-1,4-dioxaspiro[4.5]decane and 13.2 g of triethylamine are dissolved in 100 ml of dry ether. To this solution 10.2 g of acetyl chloride are dropped with cooling the solution to about 10° C. The reaction is completed by heating the solution for 3 hours under reflux. After cooling, the formed hydrochloride of triethylamine is filtered off and the ethereal filtrate is evaporated. Molecular distillation of the residue yields 8-aza-2-acetoxymethyl-6,7,9-trimethyl-7,9-diethyl-1,4-dioxaspiro[4.5]decane (Compound No. 12). which distills at 115° C/0.005 mm Hg.

By carrying out the same procedure but using instead of acetyl chloride the equivalent amounts of lauroyl chloride, sebazoyl dichloride or terephthaloyl dichloride there are obtained 8-aza-2-lauroyloxymethyl-6,7,9-trimethyl-7,9-diethyl-1,4-dioxaspiro[4.5]decane (Compound No. 13), distilling at 125° C/0.005 mm Hg; bis(8-aza-6,7,9-trimethyl-7,9-diethyl-1,4-dioxaspiro[4.5]decyl-2-methyl)sebacate (Compound No. 14), and bis(8-aza-6,7,9-trimethyl-7,9-diethyl-1,4-dioxaspiro[4.5]decyl-2-methyl)terephthalate (Compound No. 15) respectively. Compounds No. 14 and 15 can be purified by chromatography.

EXAMPLE 5

24.1 g of 8-aza-6,7,9-trimethyl-7,9-diethyl-1,4-dioxaspiro [4.5]decane are dissolved in 100 ml methylene chloride. Into this solution is dropped a solution of 42.6 g of m-chloroperbenzoic acid in 300 ml methylene chloride within 2 hours. The reaction mixture becomes red and m-chlorobenzoic acid is precipitating gradually. After stirring the mixture for 12 hours the precipitate is filtered off by suction. The filtrate is washed with 200 ml of 2 n sodium hydroxide followed by 200 ml of water. After drying over sodium sulfate the methylene chloride is evaporated and the residue is distilled in vacuo. At 120° C at 0.65 mm Hg there distills pure 8-aza-6,7,9-trimethyl-7,9-diethyl-1,4-dioxaspiro[4.5]decane-8-oxyl (Compound No. 16).

EXAMPLE 6

25.5 g of 8-aza-2,6,7,9-tetramethyl-7,9-diethyl-1,4-dioxaspiro[4.5]decane, 20 g of acetic anhydride, 14 g of calcined potash (as fine powder) and 200 ml of toluene are stirred for 24 hours at 105°–110° C. After this time the evolution $CO_2$ has ceased. The reaction mixture is then cooled to room temperature and 50 ml of water are added. The two layers are separated and the toluene solution is dried over $Na_2SO_4$ and evaporated. The resulting residue is distilled in vacuo yielding 8-aza-8-acetyl-2,6,7,9-tetramethyl-7,9-diethyl-1,4-dioxaspiro[4.5]decane, boiling at 137°–140° C/0.75 mm Hg (Compound No. 17).

EXAMPLE 7

48 g of 8-aza-6,7,9-trimethyl-7,9-diethyl-1,4-dioxaspiro[4.5]decane (compound No. 1), 71 g of methyl iodide and 62 g of calcined potash are stirred in 250 ml of dimethylformamide at 45° C for 20 hours. The red reaction mixture is diluted with 500 ml of toluene and washed with 300 ml of water. The separated toluene solution is dried over sodium sulfate and evaporated. High-vacuum distillation of the residue yields the 8-aza-6,7,8,9-tetramethyl-7,9-diethyl-1,4-dioxa-spiro[4.5]decane (compound No. 18) boiling at 77°–80° C/0.1 mm Hg.

EXAMPLE 8

48 g of 8-aza-6,7,9-trimethyl-7,9-diethyl-1,4-dioxaspiro[4.5]decane (compound No. 1) is stirred with 200 ml acetic acid anhydride at 85°–90° C for 5 days. The formed acetic acid and the excess of anhydride is distilled off, the residue is dissolved in 300 ml of toluene, the toluene solution is washed three times with 100 ml of water, dried over $Na_2SO_4$ and evaporated. High-vacuum distillation of the residue yields the 8-aza-8-acetyl-6,7,9-trimethyl-7,9-diethyl-1,4-dioxa-spiro[4.5]-decane (compound No. 19) boiling at 120°–122° C/0.007 mm Hg.

EXAMPLE 9

100 parts polypropylene powder (Moplen, fibre grade, Montedison Comp.) and 0.2 parts octadecyl β-(3,5-di-tert.butyl-4-hydroxyphenyl)-propionate as antioxidant and 0.25 parts of a light stabilizer listed in the Table are homogenised in a Brabender plastograph during 10 minutes at 200° C. The resulting mass is pressed to a 2 to 3 mm thick sheet in a laboratory press. The sheet is hot pressed in a hydraulic press during 6 minutes at 260° C and a pressure of 12 tons yielding a 0.5 mm thick film which is quenched immediately in cold water. By the same procedure a 0.1 mm film is made from the 0.5 mm film.

Test specimens of 66 × 44 mm are cut from the film and irradiated in a "Xenotest 150" radiation equipment. The content of carbonyl groups of the irradiated films is periodically controlled by infrared spectroscopy. The increase of carbonyl groups characterised by the infrared extinction at 5.85 μ is a relevant measure for the light-induced deterioration of polypropylene (see L. Balaban et al., J. Polymer Sci., Part C, 22 (1969)m 1059–1071) and is, according to experience, accompanied by a gradual loss of the mechanical properties of the polymer. The time to reach a carbonyl extinction of 0.30 at which the control sample is brittle was taken as a measure of the effectiveness of the stabilizers. The protective action of the different light-stabilizers of the invention is shown in Table 1.

Table

| Compound (No. given in Examples 1-8) | Irradiation time (hours) to 0,30 carbonyl extinction |
|---|---|
| Series I | |
| none | 1050 |
| No. 1 | 3410 |
| 2 | 3400 |
| 3 | 2850 |
| Series II | |
| none | 950 |
| No. 9 | 5300 |
| 12 | 4540 |
| 13 | 4430 |

What we claim is:

1. Compounds of the formula I $$\left[ \begin{array}{c} R^1 \quad R^2 \quad R^6 \\ X-N \quad \underset{R^3 \quad R^4 \quad R^5}{\diagdown} \underset{O}{\overset{O}{\diagup}} Y \end{array} \right]_n \quad I$$

or mixtures of isomers thereof or acid addition salts thereof, wherein $n$ is 1 or 2, $R^1$ is ethyl, $R^2$ is alkyl having 1-6 C-atoms, $R^3$ is ethyl, phenyl, benzyl or phenethyl, $R^4$ is alkyl having 1-6 C-atoms, or $R^3$ and $R^4$ together with the C-atom to which they are attached represent a cyclopentyl or cyclohexyl group, $R^5$ is alkyl having 1-5 C-atoms, alkenyl or alkinyl having 3-4 C-atoms or aralkyl having 7-8 C-atoms, $R^6$ is hydrogen, alkyl having 1-5 C-atoms, alkenyl or alkinyl having 3-4 C-atoms, aralkyl having 7-8 C-atoms and $R^5$ and $R^6$ are interchangeable, X is hydrogen, the oxyl radical, alkyl having 1-8 C-aroms, alkenyl having 3-6 C-atoms, alkinyl having 3-6 C-atoms, alkoxyalkyl having 2-21 C-atoms, aralkyl having 7-8 C-atoms, the 2,3-epoxypropyl group, an aliphatic acyl group having 1-12 C-atoms, or one of the groups —CH$_2$COOR$^7$, —CH$_2$—CH(R$^8$)—OR$^9$ or —COOR$^{10}$ wherein $R^7$ is alkyl having 1-12 C-atoms, alkenyl having 3-6 C-atoms, phenyl, aralkyl having 7-8 C-atoms or cyclohexyl, $R^8$ is H, CH$_3$ or phenyl, $R^9$ is H or an aliphatic, aromatic, araliphatic, or alicyclic acyl group having up to 18 C-atoms, which may optionally be substituted in its aryl moiety with chlorine, alkyl having 1-4 C-atoms, alkoxy having 1-8 C-atoms and/or hydroxy, $R^{10}$ is alkyl having 1-12 C-atoms, benzyl, phenyl or cyclohexyl and if $n$ is 1, Y is one of the groups —C(R$^{11}$) (R$^{12}$)—CH(R$^{13}$)—, o-phenylene,
—CH(R$^{11}$)—CH$_2$—C(R$^{12}$) (R$^{13}$)—, —CH(R$^{12}$)—CH$_2$—C(R$^{11}$) (R$^{13}$)—,
—CH$_2$—C(R$^{11}$) (R$^{12}$)—CH(R$^{13}$)—, wherein R$^{11}$ is hydrogen, methyl or —CH$_2$OR$^{14}$, $R^{12}$ is hydrogen, methyl or ethyl, $R_{13}$ is hydrogen, methyl or ethyl, $R^{14}$ is hydrogen or a monovalent acyl residue derived from an aliphatic, cycloaliphatic, aromatic or araliphatic monocarboxylic acid having up to 18 C-atoms, which may be substituted in its aryl moiety with halogen, hydroxy and/or lower alkyl groups, or R$^{14}$ is alkyl having 1-4 C-atoms, alkenyl having 3 or 4 C-atoms, benzyl or a carbamoyl residue —CO—NH—R$^{15}$ wherein R$^{15}$ is alkyl having 1-12 C-atoms, cyclohexyl, aralkyl having 7 or 8 C-atoms or aryl having 6-12 C-atoms, and if $n$ is 2

Y is one of the groups $$-CH_2 \qquad CH_2- \\ | \qquad\qquad | \\ -CH-CH_2-O-R^{16}-O-CH_2-CH \quad,$$

$$\begin{array}{c} -CH_2 \diagdown \diagup CH_2 \\ C \\ -CH_2 \diagup \diagdown CH_2- \end{array} \quad \text{or}$$

$$\begin{array}{c} -CH_2 \diagdown \underset{R^{12}}{\phantom{x}} \qquad\qquad R^{12} \underset{\phantom{x}}{\phantom{x}} \diagup CH_2- \\ C-CH_2-O-R^{16}-O-CH_2-C \\ -CH_2 \diagup \qquad\qquad\qquad\qquad \diagdown CH_2- \end{array}$$

wherein R$^{16}$ is a divalent acyl residue derived from an aliphatic, aromatic or araliphatic dicarboxylic acid having up to 12 C-atoms or R$^{16}$ is a dicarbamoyl residue —CONH—R$^{17}$—NHCO—, wherein R$^{17}$ is alkylene having 2-8 C-atoms, arylene having 6-12 C-atoms, xylylene or methanediphenylene.

2. Compounds according to claim 1 of formula I, wherein R$^5$ is alkyl and R$^6$ is alkyl or hydrogen and the number of C-atoms of R$^5$ is one less than that of R$^1$ and the number of C-atoms of R$^6$ is one less than that of R$^2$.

3. Compounds according to claim 2 of formula I, wherein R$^1$ and R$^3$ are ethyl groups, R$^2$, R$^4$ and R$^5$ are methyl groups and R$^6$ is hydrogen.

4. Compounds according to claim 3 of formula I, wherein X is hydrogen, oxyl or methyl.

5. Compounds according to claim 3 of formula I, wherein X is acetyl, acryloyl or crotonoyl.

6. Compounds according to claim 3 of formula I, wherein $n$ is 1 and Y is a group —CH$_2$—CH(R$^{11}$)— or —CH$_2$—C(R$^{11}$) (R$^{12}$)—CH$_2$—, wherein R$^{11}$ is H, CH$_3$ or CH$_2$OR$^{14}$, R$^{12}$ is H, CH$_3$ or C$_2$H$_5$ and R$^{14}$ is H, an aliphatic acyl residue having 2-12 C-atoms, a benzoyl residue which may be substituted with alkyl having 1-4 C-atoms and/or hydroxy, or R$^{14}$ is a $\beta$(3,5-di-tert.butyl-4-hydroxyphenyl)propionyl group.

7. Compounds according to claim 3 of formula I, wherein $n$ is 2 and Y is the group (—CH$_2$)$_2$C(CH$_2$—)$_2$.

8. The compound according to claim 1, 8-aza-6,7,9-trimethyl-7,9-diethyl-1,4-dioxa-spiro[4.5]decane.

9. The compound according to claim 1, 9-aza-3,3,7,8,10-pentamethyl-8,10-diethyl-1,5-dioxa-spiro[5.5]undecane.

10. The compound according to claim 1, 9-aza-3,3,7,8,9,10-hexamethyl-8,10-diethyl-1,5-dioxa-spiro[5.5]undecane.

11. The compound according to claim 1, 8-aza-2-lauroyloxymethyl-6,7,9-trimethyl-7,9-diethyl-1,4-dioxa-spiro[4.5]decane.

12. The compound according to claim 1, 8-aza-2-hydroxymethyl-6,7,9-trimethyl-7,9-diethyl-1,4-dioxa-spiro[4.5]decane.

13. A method of stabilizing organic polymers against light-induced deterioration, consisting in the addition of 0.01 to 5% by weight of a compound of formula I as defined in claim 1 to the polymer.

14. A method according to claim 13, wherein the organic polymer is a polyolefin or a styrene homo- or copolymer.

15. A method according to claim 13, wherein the organic polymer is a polyurethane or polyamide.

16. A composition of matter stabilized against light-induced deterioration comprising an organic polymer, normally subject to deterioration by light, and 0.01 to 5% by weight of a compound of formula I according to claim 1.

17. A composition according to claim 16, wherein the organic polymer is a polyolefin or a styrene homo- or co-polymer.

18. A composition according to claim 16, wherein the organic polymer is a polyurethane or polyamide.

19. A method according to claim 14, containing one or more conventional phenolic antioxydants in addition to the light-stabilizer of formula I.

20. A composition of matter stabilized against light-induced deterioration comprising an organic polymer, normally subject to deterioration by light, and 0.01 to 5% by weight of a compound of claim 3.

21. A composition of matter stabilized against light-induced deterioration comprising an organic polymer, normally subject to deterioration by light, and 0.01 to 5% by weight of a compound of claim 4.

22. A composition of matter stabilizer against light-induced deterioration comprising an organic polymer, normally subject to deterioration by light, and 0.01 to 5% by weight of a compound of claim 5.

23. A composition of matter stabilized against light-induced deterioration comprising an organic polymer, normally subject to deterioration by light, and 0.01 to 5% by weight of a compound of claim 6.

24. A composition of matter stabilized against light-induced deterioration comprising an organic polymer, normally subject to deterioration by light, and 0.01 to 5% by weight of a compound of claim 7.

* * * * *